US00PP35573P2

(12) United States Plant Patent
Van Swieten

(10) Patent No.: US PP35,573 P2
(45) Date of Patent: Jan. 9, 2024

(54) ***PHALAENOPSIS* ORCHID PLANT NAMED 'PHA407209'**

(50) Latin Name: ***Phalaenopsis* hybrid**
Varietal Denomination: PHA407209

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,299

(22) Filed: Jun. 22, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA407209', particularly characterized by having attractive reddish-purple flowers with small, lighter purple edges and reddish-purple lips, flowers that are flat in lateral view, lip curvature of lateral lobe is medium, leaf symmetry of apex is strongly asymmetric, and is propagated by meristem tissue culture, is disclosed.

3 Drawing Sheets

Genus and species: *Phalaenopsis* hybrid.
Variety denomination: 'PHA407209'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA407209'.

The new *Phalaenopsis* plant is a product of a planned breeding program conducted by the inventor in Bleiswijk, the Netherlands. The objective of this breeding program was to create a new *Phalaenopsis* plant with numerous attractive reddish-purple flowers with small, lighter purple edges, and reddish-purple lips, suitable for potted plant production.

The new *Phalaenopsis* plant 'PHA407209' is a result of cross-pollination made by the inventor in March 2013 in Bleiswijk, the Netherlands, of the proprietary female, or seed parent, *Phalaenopsis* hybrid '00001-4992' (unpatented) with the proprietary male, or pollen parent, *Phalaenopsis* hybrid '12-050832-0002' (unpatented).

The new *Phalaenopsis* was selected by the inventor as a single plant within the progeny of the stated cross-pollination in a controlled greenhouse in Bleiswijk, the Netherlands, in December 2017. Asexual reproduction of the new *Phalaenopsis* plant by meristem tissue culture since 2019 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 20, 2022 (Application no. 2022/0184), by Applicant who obtained the subject matter disclosed directly from the inventor. 'PHA407209' has not been made publicly available or sold anywhere in the world prior to the effective filing date of this application with the exception of sales or disclosures made one year or less before the effective filing date of this claimed invention by Applicant who obtained 'PHA407209' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA407209' as a new and distinct variety of *Phalaenopsis* plant:

1) reddish-purple flowers with small lighter purple edges and reddish-purple lips;
2) flower shape in lateral view is flat;
3) lip curvature of lateral lobes is medium; and
4) strongly asymmetric leaf symmetry of apex.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2023. Colors in the photographs may differ from the color values cited in the detailed botanical description, which accurately describe the actual colors of the new variety.

DESCRIPTION OF THE NEW VARIETY

Figure 1:
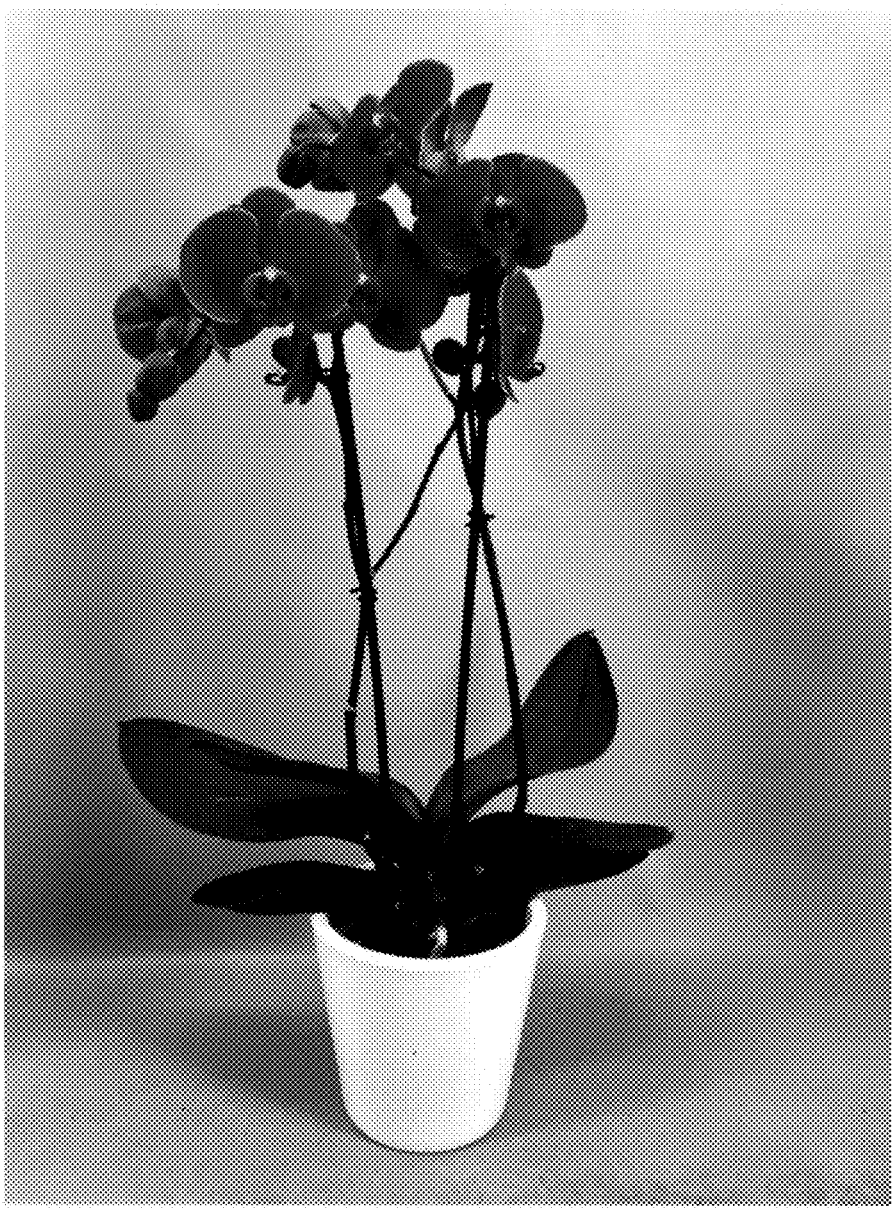
FIG. 1 shows the overall plant habit, including blooms, buds, and foliage of 'PHA407209'.
Figure 2:
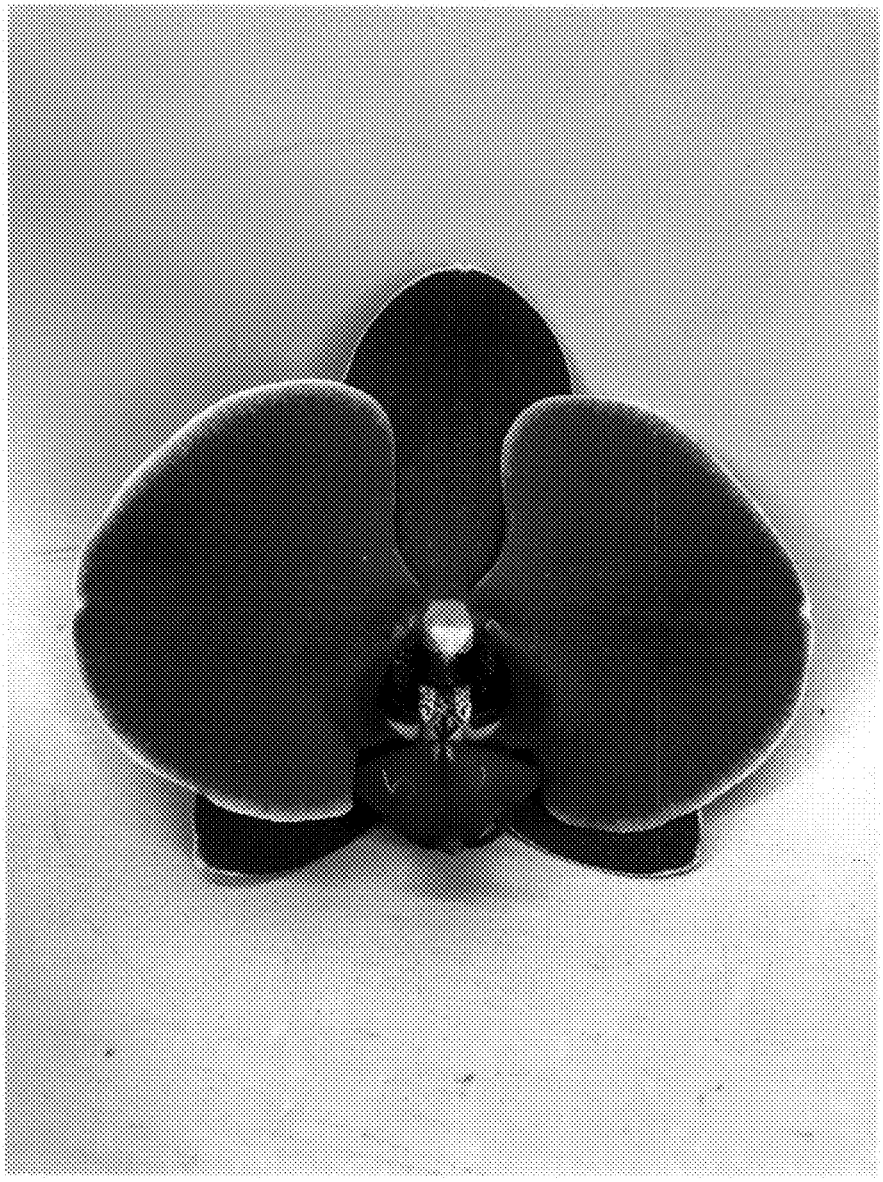
FIG. 2 shows a close-up of a flower of 'PHA407209'.
Figure 3:
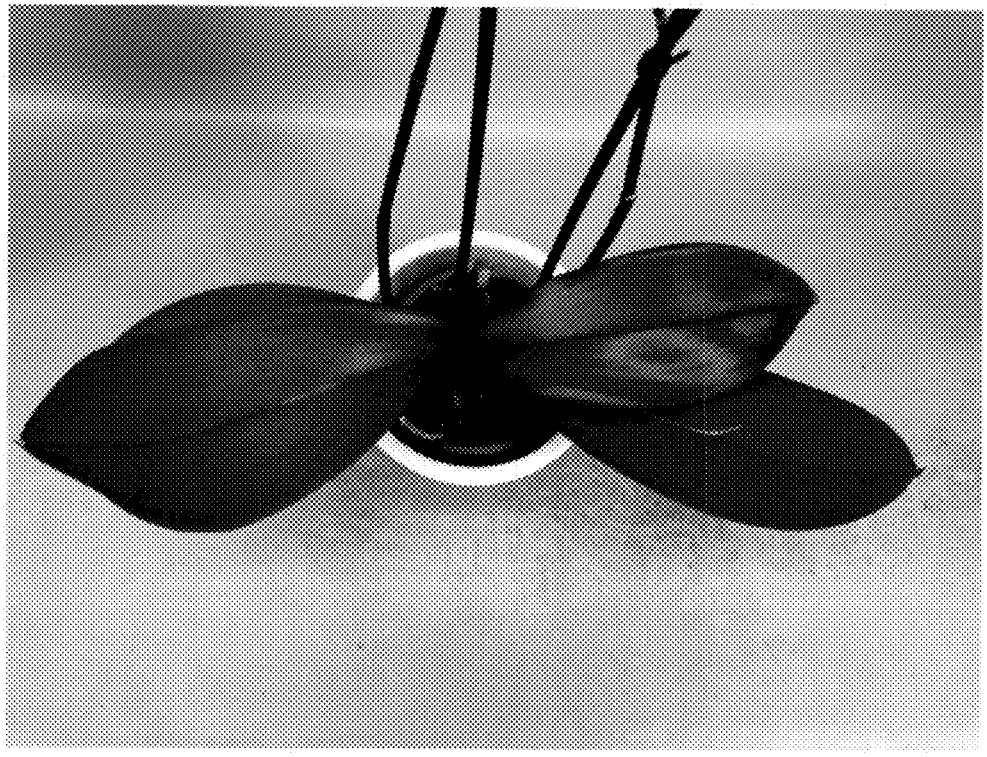
FIG. 3 shows an overhead, close-up view of the leaves of 'PHA407209'.

The following detailed description sets forth the distinctive characteristics of 'PHA407209'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHA407209'.

Parentage:

*Female parent*.—*Phalaenopsis* cultivar '00001-4992' (unpatented).

*Male parent*.—*Phalaenopsis* cultivar '12-050832-0002' (unpatented).

Propagation:

*Type*.—Meristem tissue culture.

Roots:

*Root description*.—Greyed-green colored roots (a color in between RHS 190B and RHS 190C) with branching lateral roots having yellow-green (RHS 145B) with a touch of purplish-red colored root tips (RHS N77B).

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height* (*from soil level to top of inflorescence*).—Approximately 52.0 cm to 57.0 cm.

*Width* (*measured from leaf tips*).—About 31.0 cm to 33.0 cm.

*Vigor*.—Strong.

Leaves:

*Mature leaves*.—Quantity per plant: 8 to 10 leaves are produced before flowering. Length (fully expanded): 18.0 cm to 20.0 cm. Width: 8.5 cm to 9.5 cm. Position of the broadest part of the leaf: Toward the tip. Shape: Obovate. Base shape: Moderately elongated. Apex: Acute asymmetric. Leaf blade angle with the petiole (measured from the horizontal position): Between 30 degrees and 45 degrees. Leaf margin: Entire. Color: Upper surface: Green (RHS 146A) with a reddish-brown margin (RHS 200B) toward the tip. Lower surface: Green (RHS 146B) with a purple margin (RHS N77A) toward the tip. Texture (both upper and lower surfaces): Smooth. Thickness: 2.0 mm to 3.0 mm. Variegation: Absent. Venation: Pattern: Parallel. Color of the midvein: Upper surface: Green (RHS 147A). Lower surface: Purple (RHS N77A).

Peduncle:

*Quantity per plant*.—2.

*Number of flowers per peduncle*.—10 to 13.

*Length*.—52.0 cm to 57.0 cm.

*Diameter*.—5.0 mm to 6.0 mm.

*Strength*.—Strong.

*Aspect*.—Upright to slightly pendent.

*Texture*.—Smooth.

*Color*.—Mix of brown (RHS 200A) and green (RHS 194A).

*Internode length*.—3.0 cm to 3.5 cm.

Inflorescence description:

*Appearance*.—Upright to slightly pendent, panicle inflorescence with bilaterally symmetrical flowers that open in succession beginning with the lowermost flower.

*Number of inflorescences*.—2.

*Inflorescence size*.—Height (from base to tip): 200.0 mm to 240.0 mm.

*Flowering time*.—First flowers can be expected 10 to 11 months after planting in a 12-cm pot.

*Flower*.—Height: 75.0 mm to 80.0 mm. Diameter: 85.0 mm to 90.0 mm. Depth of lip: 23.0 mm to 25.0 mm.

*Flower shape*.—Flat.

*Flower longevity*.—On the plant: 9 to 11 weeks.

*Fragrance*.—Absent.

*Flower bud*.—Average size: Large. Length: 24.0 mm to 26.0 mm. Width: 23.0 mm to 25.0 mm. Shape: Egg shaped. Color: Touch of yellow-green (RHS 145C) at the base; purplish-red (RHS N77B) with a touch of dark purplish-red (RHS N79C) toward the tip.

*Petals*.—Arrangement: Open/free. Shape: Moderately compressed. Apex: Emarginated asymmetric. Margin: Entire. Length (from base to tip): 41.0 mm to 43.0 mm. Width: 54.0 mm to 56.0 mm. Position of the broadest part of the petal: Toward the base. Color (when fully opened): Upper surface: Basic color: Reddish-purple (RHS N78A). Over color: Small, light purple edge (RHS 76A); very small number of very light purple dots (RHS 76B). Lower surface: Basic color: Purplish-pink (RHS N78C). Over color: Reddish-purple (RHS N78B). Number of spots, dots, and stripes on the petals (upper surface): Medium very small dots. Color of spots, dots, and stripes on the petals (upper surface): RHS 76B. Density of netting of the petals (upper surface): None. Color of the netting (upper surface): Not applicable.

*Dorsal sepal*.—Shape: Elliptic. Apex: Emarginated symmetric. Margin: Entire. Length (from base to tip): 41.0 mm to 43.0 mm. Width: 31.0 mm to 34.0 mm. Position of the broadest part of the dorsal sepals: At the middle. Color (when fully opened): Upper surface: Basic color: Reddish-purple (RHS N78A). Over color: Very small white edge (RHS NN155C) and very small number of very light purple dots (RHS 76B). Lower surface: Basic color: Purplish-pink (RHS N78C). Over color: Very light purple dots (RHS 76C). Number of spots, dots, and stripes on the dorsal sepals (upper surface): Many to very many dots scattered all over sepals. Color of spots, dots, and stripes on the dorsal sepals (upper surface): RHS 76B. Density of netting of the dorsal sepals (upper surface): None. Color of the netting (upper surface): None.

*Lateral sepals*.—Shape: Ovate. Apex: Obtuse asymmetric. Margin: Entire. Length (from base to tip): 40.0 mm to 42.0 mm. Width: 27.0 mm to 29.0 mm. Position of the broadest part of the lateral sepals: Toward the base. Color (when fully opened): Upper surface: Basic color: Reddish-purple (RHS N78A). Over color: Light yellow-green (RHS 145C) and dotted (RHS 59A) at the base; very light purple dots (RHS 76B) scattered all over sepals. Lower surface: Basic color: Reddish-purple (RHS N78B). Over color: Light yellow-green (RHS 145D) at the base; reddish-purple midvein (RHS N78A). Number of spots, dots, and stripes on the lateral sepals (upper surface): Medium number of small dots at the base and many very small dots scattered all over sepals. Color of spots, dots, and stripes on the lateral sepals (upper surface): RHS 59A at the base and RHS 76B all over the sepals. Density of netting of the lateral sepals (upper surface): None. Color of the netting (upper surface): Not applicable.

*Labellum* (*lip*).—Whiskers: Present. Length of whiskers: 18.0 mm to. 20.0 mm. Color of whiskers: Reddish-purple (RHS N78A); red margin (RHS 59A) on one side; very light purple tips (RHS 76C). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Moderately undulated. Length: 20.0 mm to 22.0 mm. Width: 14.0 mm to 16.0 mm. Color: Upper surface: Pinkish-white (RHS N155B) at the base and on one side; red stripes (RHS 183B) at the base; red (RHS 187C) on one side; reddish-purple (a color from RHS N78A to RHS N78B) toward the tip. Lower surface: White (RHS 155C) at the base; red (RHS 187C) on one side; purplish-pink (RHS N78C) toward the tip. Number of spots and stripes on the lateral lobe: Few stripes. Color of spots and stripes on the lateral lobe: RHS 183B. Density of netting of the lateral lobe: None. Color of the netting: None.

*Apical lobe*.—Shape: Triangular. Margin: Entire. Length: 19.0 mm to 21.0 mm. Width: 21.0 mm to 23.0 mm. Color: Upper surface: Light greenish-yellow (RHS 5C); red (RHS 185B) at the base and toward wings; reddish-purple (RHS N78A) shaded at the middle and toward whiskers RHS 59B. Lower surface: Red margin (RHS 185A); reddish-purple (RHS N78B) toward whiskers. Number of spots and stripes on the apical lobe: None. Color of spots and stripes on the apical lobe: None. Density of netting of the apical lobe: None. Color of the netting: None. Bump and ridge: Absent.

*Callus*.—Average size: Medium. Height: 6.0 mm to 7.0 mm. Length: 6.0 mm to 7.0 mm. Width: 5.0 mm to 6.0 mm. Color: Light greenish-yellow (RHS 5C) at the base; white (RHS 155C) on sides; purplish-red flecks (RHS 59B).

Reproductive organs:

*Column*.—Length: 8.0 mm to 9.0 mm. Diameter: 5.0 mm to 6.0 mm. Color: Purplish-pink (RHS N78C) with reddish-purple stripe (RHS N78B) from base toward the tip.

*Pollinia*.—Quantity: 2. Diameter: 1.0 mm to 1.2 mm. Color: Orange-yellow (RHS 23A).

*Ovary*.—Length: 10.0 mm to 12.0 mm. Diameter: 2.4 mm to 2.7 mm.

*Pedicel*.—Length: 37.0 mm to 39.0 mm. Diameter: 2.8 mm to 3.1 mm. Color: Touch of dark brown (RHS N200A) and purplish-red (RHS N77B) at the base; light yellow-green (RHS 195C) with a touch of light reddish-purple (RHS N78D) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA407209' differs from the female parent plant '00001-4992' (unpatented) in that 'PHA407209' has free arrangement of petals, medium-length whiskers, and semi-erect leaf attitude, whereas '00001-4992' has touching arrangement of petals, short whiskers, and erect to semi-erect leaf attitude.

'PHA407209' differs from the male parent plant '12-050832-0002' (unpatented) in that 'PHA407209' has semi-erect leaf attitude, strong symmetry of apexes, and emarginated dorsal sepals, whereas '12-050832-0002' has horizontal to semi-drooping leaf attitude, moderate symmetry of apexes, and obtuse dorsal sepals.

'PHA407209' is most similar to the commercial *Phalaenopsis* plants named 'PHA329719' (U.S. Plant Pat. No. 34,550) and 'PHA393573' (U.S. Plant Pat. No. 34,519). 'PHA407209' differs from the commercial variety 'PHA329719' in that 'PHA407209' has strongly asymmetric leaf apexes, medium whiskers, and no stripes on petals, whereas 'PHA329719' has symmetric or slightly asymmetric leaf apexes, short to medium whiskers, and few stripes on petals.

'PHA407209' differs from the commercial variety 'PHA393573' in that 'PHA407209' has triangular apical lobes, semi-erect leaf attitude, and purplish-pink columns, whereas 'PHA393573' has trullate apical lobes, horizontal to semi-drooping leaf attitude, and reddish-purple columns.

I claim:

1. A new and distinct variety of *Phalaenopsis* plant named 'PHA407209', substantially as described and illustrated herein.

* * * * *